United States Patent
Fan et al.

(10) Patent No.: US 11,965,010 B2
(45) Date of Patent: Apr. 23, 2024

(54) METHOD FOR PREPARING A PORCINE-DERIVED INTERFERON-DELTA 5 AND APPLICATION OF PORCINE-DERIVED INTERFERON-DELTA 5

(71) Applicant: Jiangsu Academy of Agricultural Sciences, Nanjing (CN)

(72) Inventors: Baochao Fan, Nanjing (CN); Bin Li, Nanjing (CN); Shiying Song, Nanjing (CN); Xuehan Zhang, Nanjing (CN); Xuejiao Zhu, Nanjing (CN); Jinzhu Zhou, Nanjing (CN); Yongxiang Zhao, Nanjing (CN); Jizong Li, Nanjing (CN); Rongli Guo, Nanjing (CN); Weilu Guo, Nanjing (CN); Xue Zhang, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 0 days.

(21) Appl. No.: 18/308,512

(22) Filed: Apr. 27, 2023

(65) Prior Publication Data

US 2023/0303651 A1    Sep. 28, 2023

Related U.S. Application Data

(63) Continuation of application No. PCT/CN2022/111968, filed on Aug. 12, 2022.

(30) Foreign Application Priority Data

Feb. 24, 2022    (CN) .......................... 202210191044.1

(51) Int. Cl.
   *C07K 14/555*    (2006.01)
(52) U.S. Cl.
   CPC .................... *C07K 14/555* (2013.01)
(58) Field of Classification Search
   CPC .................................................. C07K 14/555
   See application file for complete search history.

(56) References Cited

FOREIGN PATENT DOCUMENTS

| CN | 101955941 A | 1/2011 |
| CN | 103757041 A | 4/2014 |
| CN | 114525294 A | 5/2022 |

OTHER PUBLICATIONS

Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: the 70% Hurdle. Genome Research, 2000, 10:398-400 (Year: 2000).*
Hinz et al. From protein sequences to 3D-structures and beyond: the example of the UniProt Knowledgebase. Cell. Mol. Life Sci. (2010) 67:1049-1064 (Year: 2010).*
Miosge et al. Comparison of predicted and actual consequences of missense mutations. Proceedings of the National Academy of Sciences Sep. 2015, 112 (37) E5189-E5198 (Year: 2015).*
Sang et al. Differential expression and activity of the porcine type I interferon family. Physiol Genomics. Jul. 7, 2010;42(2):248-58. ( Year: 2010).*
International Search Report and Written Opinion for PCT/CN2022/111968, dated Nov. 28, 2022.
First Office Action for China Application No. 202210191044.1.
Sus scrofa interferon-delta-5 (IFN-DELTA-5), mRNA GenBank 20.2, 2022 (Feb. 20, 2022), NM_01164854.
Elisabetta Razzuoli et al., "The Swine IFN System in Viral Infections: Major Advances and Translational Prospects," Pathogens, Jan. 27, 2022, 11, 175.
Yongming Sang et al., "Differential expression and activity of the porcine type I interferon family," Physiol Genomics, Apr. 20, 2010, pp. 248-258, vol. 42.
Li Hong et al., "Construction and High Level Expression of Prokaryotic Expression Vector of Pig Interferon-δ Gene," China Animal Husbandry & Veterinary Medicine, Dec. 2016, pp. 940-945, vol. 43.

(Continued)

*Primary Examiner* — Vanessa L. Ford
*Assistant Examiner* — Sandra Dillahunt
(74) *Attorney, Agent, or Firm* — Piloff Passino & Cosenza LLP; Sean A. Passino; Rachel K. Piloff

(57) ABSTRACT

Disclosed are a method for preparing a porcine-derived interferon-delta 5 (pIFN-δ5) and an application of the pIFN-δ5, where the method for preparing pIFN-δ5 includes the following steps: step S1, obtaining a DNA fragment containing pIFN-δ5 gene through reverse transcription-polymerase chain reaction (RT-PCR) amplification by using the total RNA of pretreated porcine small intestinal epithelial cells IPEC-J2; step S2, inserting the DNA fragment containing pIFN-δ5 gene into an exogenous expression vector to construct a recombinant expression vector for expressing the pIFN-δ5 gene; and step S3, introducing the recombinant expression vector into a suitable host cell, and driving the host cell to express the pIFN-δ5 gene to obtain the pIFN-δ5. The recombinant pIFN-δ5 protein is used to prepare drugs or preparations for inhibiting infection of porcine epidemic diarrhea virus (PEDV), porcine transmissible gastroenteritis virus (TGEV), porcine delta coronavirus (PDCoV) and porcine rotavirus (PRoV).

1 Claim, 6 Drawing Sheets

Specification includes a Sequence Listing.

(56) References Cited

OTHER PUBLICATIONS

Interferon-delta-5 precursor [Sus scrofa], GenBank NP_001158326. 1.
Notice of Registration for China Application No. 202210191044.1, dated Nov. 30, 2022.

\* cited by examiner

SEQUENCE LISTING

```
Sequence total quantity: 4
SEQ ID NO: 1           moltype = DNA  length = 555
FEATURE                Location/Qualifiers
source                 1..555
                       mol_type = other DNA
                       organism = synthetic construct
SEQUENCE: 1
atggcccaca tccatttgct cctggcaggg gtgatactct cctccattgc tgctggcact  60
cttggccaat tctctgggat ccataggtta gagaacaggg aaatcttcat gcttttaaga  120
cagatgaaaa ggatctcctc tcaggcatgc ctaaaggaca gaactgactt ccaatttcct  180
tggaaaggag gcaaaaccac cagaacacag acatctcaag gcacctgttt ccaccctctg  240
atgctccagc agatcatcaa cctcttcaac acagagaaca gccgggctgc ttggaacaac  300
gccctcctcg atcaactact ctctcgcctt gatcacggcc tggaccgact agagcagatg  360
gaaggtgaca atctggcttg tgcctatttg ggaagtgttg tccggaaata tttccaaaga  420
atccatcgct atctcaaaaa gaaggaatat agttcctgtg cctgggaggt tgtcagagta  480
gaaactgaag tgtgcctttc ccttatgcaa caatcgtcaa cgaagagtca agagagaaaa  540
aaggcacact tgtga                                                   555

SEQ ID NO: 2           moltype = AA  length = 162
FEATURE                Location/Qualifiers
source                 1..162
                       mol_type = protein
                       organism = synthetic construct
SEQUENCE: 2
QFSGIHRLEN REIFMLLRQM KRISSQACLK DRTDFQFPWK GGKTTRTQTS QGTCFHPLML  60
QQIINLFNTE NSRAAWNNAL LDQLLSRLDH GLDRLEQMEG DNLACAYLGS VVRKYFQRIH  120
RYLKKKEYSS CAWEVVRVET EVCLSLMQQS STKSQERKKA HL                     162

SEQ ID NO: 3           moltype = DNA  length = 30
FEATURE                Location/Qualifiers
source                 1..30
                       mol_type = other DNA
                       organism = synthetic construct
SEQUENCE: 3
gcgatatcca attctctggg atccataggt                                   30

SEQ ID NO: 4           moltype = DNA  length = 31
FEATURE                Location/Qualifiers
source                 1..31
                       mol_type = other DNA
                       organism = synthetic construct
SEQUENCE: 4
cgaagcttca agtgtgcctt ttttctctct t                                 31
```

US 11,965,010 B2

METHOD FOR PREPARING A PORCINE-DERIVED INTERFERON-DELTA 5 AND APPLICATION OF PORCINE-DERIVED INTERFERON-DELTA 5

CROSS-REFERENCE TO RELATED APPLICATIONS

This application is a continuation of PCT/CN2022/111968, filed Aug. 12, 2022, and claims priority of Chinese Patent Application No. 202210191044.1, filed on Feb. 24, 2022, the entire contents of each of which are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:
File name: 347_001_sequence
Creation date: Apr. 20, 2023
Byte size: 5, 386

TECHNICAL FIELD

The present application belongs to the technical field of preparing genetic engineering products, and particularly relates to a method for preparing a porcine-derived interferon-delta 5 (pINF-δ5) and application of the pINF-δ5.

BACKGROUND

Porcine virus diarrhea is a serious epidemic affecting the livestock industry, with particularly severe effects on newborn piglets, and losses due to diarrhea of up to 10 billion Chinese yuan per year. There are many different pathogens that cause viral diarrhea in pigs, with porcine epidemic diarrhea virus (PEDV), porcine transmissible gastroenteritis virus (TGEV), porcine delta coronavirus (PDCoV) and porcine rotavirus (PRoV) being the most important pathogens in clinical practice, some of which are 100 percent (%) fatal to newborn piglets.

Interferon (IFN) plays an increasingly important role in the fight against viral infections, as it is the first line of defense against viral infections. Mainly, IFN induces the expression of antiviral proteins, which then further activate the immune response against the virus and regulate the cellular response. Generally, IFN is divided into three subtypes based on the structure of the cell surface receptors: type I, type II and type III. Among them, type I IFN includes IFN-alpha (α), IFN-beta (β), IFN-epsilon (ε), IFN-ω (omega), IFN-κ (kappa), IFN-δ (delta), IFN-τ (tau) and IFN-ζ (xi), with direct effects in the antiviral immune response.

IFN-δ was first identified by Lefevre and Boulay in 1993 as a member of type I IFN, and it was not until recent years that Cochet et al. reported several sequences related to different isoforms of IFN-δ through a genomic database screen, suggesting that IFN-δ is present in numerous even-toed ungulates and forms a distinct cluster in the genome. Studies have shown that there are 11 porcine-derived IFN-δ isoforms, ranging from IFN-δ1 to IFN-δ11, and that several porcine INF-δ isoforms are relatively highly expressed in the gestation phase of the sow and the intestine of the piglet, indicating that IFN-δ is likely to play an important anti-infective role in the neonatal phase of the piglet.

Currently, there are no technical studies on large-scale preparation of porcine-derived IFN-δ5 (pIFN-δ5), and the applications of pIFN-δ5 in the suppression of viral diarrheal pathogens in porcine are thus limited.

SUMMARY

To this end, the present application provides a method for preparing a porcine-derived interferon delta-5 (pIFN-δ5) so as to overcome the shortcomings and deficiencies of the prior art.

The method for preparing a pIFN-δ5 includes steps as follows:
  step S1, obtaining a deoxyribonucleic acid (DNA) fragment containing pIFN-δ5 gene;
  step S2, inserting the DNA fragment containing pIFN-δ5 gene into an exogenous expression vector to construct a recombinant expression vector for expressing the pIFN-δ5 gene; and
  step S3, introducing the recombinant expression vector into a suitable host cell, and driving the host cell to express the pIFN-δ5 gene to obtain the pIFN-δ5.

Optionally, the DNA fragment containing pIFN-δ5 gene has a sequence as set forth in SEQ ID NO: 1 or a DNA sequence with more than 80% homology with the DNA fragment containing pIFN-δ5 gene.

Optionally, in the step S1, small intestinal epithelial cells IPEC-J2 are pretreated by inducing and culturing with polyinosinic: polycytidylic acid (Poly I:C) or by infecting with porcine viral diarrhea pathogens, and the pretreated small intestinal epithelial cells IPEC-J2 are used to extract total RNA, followed by reverse transcription-polymerase chain reaction (RT-PCR) amplification by a primer P1 with a sequence of 5'-GCGATATCCAATTCTCTGGGATCCATAGGT-3' (SEQ ID NO: 3) and a primer P2 with a sequence of 5'-CGAAGCTTCAAGTGTGCCTTTTTTCTCTCTT-3' (SEQ ID NO: 4), so as to obtain the DNA fragment containing pIFN-δ5 gene.

Optionally, the exogenous expression vector in step S2 is a prokaryotic plasmid vector, preferably pET-32a(+).

Optionally, the host cell is *Escherichia coli* BL21(DE3).

Optionally, the method for preparing pIFN-δ5 further includes a step S4 of purifying the obtained pIFN-δ5 to obtain purified pIFN-δ5.

Another aspect of the present application provides a pIFN-δ5 prepared by the above method.

Another aspect of the present application provides an application of the pIFN-δ5 in preparing drugs or preparations for treating porcine viral diarrhea.

Compared with the prior art, the present application has the following advantages and effects: according to the present application, a method for preparing porcine pIFN-δ5 protein by prokaryotic expression is provided for the first time, and the pIFN-δ5 protein expressible in culture supernatant is obtained under optimized conditions; the pET vector expression system selected carries a His tag, which is convenient for further purification of the expression product; the signal peptide sequence of IFN-δ5 is removed by primer design during the construction of the prokaryotic expression vector, resulting in a higher protein expression efficiency of the recombinant expression plasmid pET-pIFN-δ5 obtained by the construction; the present application innovatively achieves the preparation and purification of pIFN-δ5 protein in large quantities, and the pIFN-δ5 protein obtained from the preparation is used to inhibit a variety of viral diarrhea causative agents in swine, thus providing a good solution for preparing drugs or preparations to treat viral diarrhea in swine.

BRIEF DESCRIPTION OF THE DRAWINGS

FIG. 1A is a diagram illustrating electrophoresis of amplified pIFN-δ5 gene and FIG. 1B shows double digestion identification of recombinant plasmid pET-pIFN-δ5, with lane M being DNA molecular weight standard DL2000 and arrows on right sides of the diagrams indicating target bands respectively.

FIG. 2A shows the expression and solubility of the target protein in Escherichia cob BL21(DE3) transformed with recombinant plasmid vector pET-pIFN-δ5 under induction conditions, whereas lane M is the protein molecular weight standard, lane 1 is a supernatant of Escherichia cob BL21(DE3) transformed with empty vector pET-32a(+) after fragmentation under induction conditions, lane 2 shows precipitates of Escherichia cob BL21(DE3) transformed with empty vector pET-32a(+) after fragmentation under induction conditions, lane 3 shows a supernatant of Escherichia cob BL21(DE3) transformed with recombinant plasmid vector pET-pIFN-δ5 cultured under non-inducing conditions after fragmentation, lane 4 shows precipitates of Escherichia cob BL21(DE3) transformed with recombinant plasmid vector pET-pIFN-δ5 cultured under non-inducing conditions after fragmentation, lane 5 shows a supernatant of Escherichia cob BL21(DE3) transformed with recombinant plasmid vector pET-pIFN-δ5 cultured under inducing conditions after fragmentation, and lane 6 shows precipitates of Escherichia cob BL21(DE3) transformed with recombinant plasmid vector pET-pIFN-δ5 after fragmentation cultured under induced conditions; and FIG. 2B shows results of detecting a target product in the supernatant of Escherichia coli BL21(DE3) transformed with the recombinant plasmid vector pET-pIFN-δ5 after fragmentation by western blot under induction conditions, where lane M is the protein molecular weight standard, lane 1 is a supernatant sample from one batch and lane 2 is a supernatant sample from another batch.

DETAILED DESCRIPTION OF THE EMBODIMENTS

The following embodiments are used to provide an exemplary description of the technical schemes of the present application and are not intended to limit the scope of the present application. If not specifically indicated, the technical methods used in the embodiments are conventional methods known to those skilled in the art and the raw materials used are commercially available items.

It is found by the inventors' team that porcine epidemic diarrhea virus (PEDV) infection induces high expression of the small intestinal interferon delta-5 (IFN-δ5) isoform in piglets, suggesting that porcine-derived IFN-δ5 (pIFN-δ5) plays an important role in resisting PEDV infection.

In the present application, reverse transcription-polymerase chain reaction (RT-PCR) is used to clone a gene of pIFN-δ5, which preferably has the DNA sequence as set forth in SEQ ID NO: 1 or a DNA sequence with more than 80 percent (%) homology to the DNA sequence as set forth in SEQ ID NO: 1. The gene based on pIFN-δ5 is expressed in the prokaryotic expression system Escherichia coli BL21 (DE3) using a recombinant method to construct a prokaryotic expression vector for the recombinant pIFN-δ5 protein, which preferably comprises an amino acid sequence as set forth in SEQ ID NO: 2 or an amino acid sequence with more than 80% homology to the amino acid sequence as set forth in SEQ ID NO: 2. Based on the fact that the pIFN-δ5 protein expressed by the above prokaryotic expression system is present in large quantities in the fragmented supernatant of the bacterium, the present application also provides a method for expressing and purifying the pIFN-δ5 protein in large quantities and applying the resulting pIFN-δ5 protein to prepare new drugs or formulations for inhibiting the causative agent of porcine viral diarrhea.

Embodiment 1 Preparation of pIFN-δ5 Protein by Prokaryotic Expression System

1. Construction of Cloning Vector

Figure 1A:
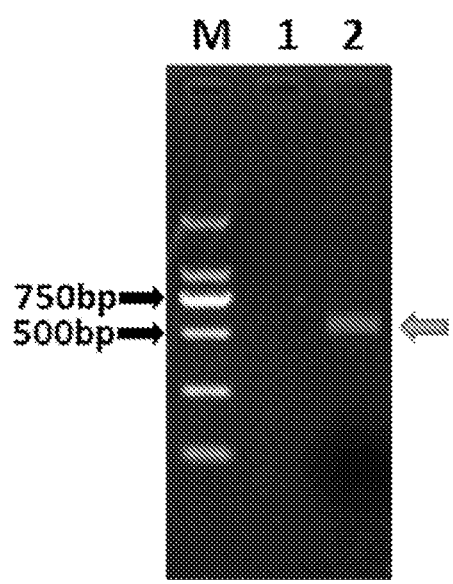
FIG. 1A and FIG. 1B are diagrams illustrating results of double digestion identification of amplified porcine-derived interferon delta-5 (pIFN-δ5) gene and recombinant plasmid, where

Firstly, the porcine small intestinal epithelial cell IPEC-J2 is infected with PEDV, and the cells infected by the virus are collected to extract total RNA by a total RNA extraction kit; specific primers are designed, including an upstream primer P1 of 5'-GCGATATCCAATTCTCTGGGATCCAT-AGGT-3' (SEQ ID NO: 3), a downstream primer P2 of 5'-CGAAGCTTCAAGTGTGCCTTTTTTCTCTCTT-3' (SEQ ID NO: 4); the gene fragment encoding pIFN-δ5 protein is subjected to RT-PCR amplification using Prime-Script RT-PCR Kit, with the primers P1, P2 and the extracted total RNA of IPEC-J2 cells as templates, where the RT-PCR amplification is carried out under reaction conditions of: 50 degrees Celsius (° C.), 30 minutes (min); 94° C., 3 min; 94° C., 30 s; 55° C., 30 s, 72° C., 40 s, and 35 cycles; then 72° C., 10 min; the amplification results are shown in FIG. 1A; further, the prokaryotic expression vector pET-32a (+) is digested with EcoRV and Hind III restriction endonucleases, and the linearized vector is recovered.

Next, the pIFN-δ5 gene fragment obtained from the above amplification is ligated to the linearized pET-32a(+) vector according to the recombinase instructions (ClonExpress®

Figure 1B:
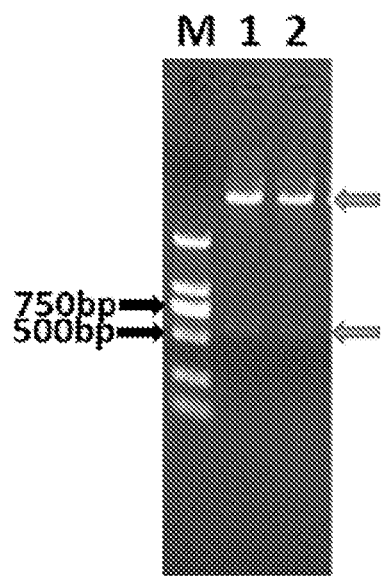

Ultra One Step Cloning Kit). The ligated product is then transformed into *Escherichia coli* DH5α receptor cells and the suspected positive clones are screened from the bacterial broth by PCR. Additional expansions are made to culture these clones and plasmids are extracted from the cultures for identification using EcoR V and Hind III double digestion, the results of which are shown in FIG. 1B; the plasmid showing correct digestion is further sequenced to obtain the recombinant plasmid pET-pIFN-δ5, where the results of sequencing suggest that the pIFN-δ5 gene fragment has the DNA sequence as set forth in SEQ ID NO: 1 and the protein expressed therein has the amino acid sequence as set forth in SEQ ID NO: 2.

2. Induced Expression and Identification of Recombinant Protein

Firstly, the recombinant plasmid pET-pIFN-δ5 is transformed into *Escherichia coli* BL21(DE3).

The positive clone BL21(DE3) containing pET-pIFN-δ5 is picked and its expression is induced by adding isopropyl-β-D-thiogalactoside (IPTG) in LB medium containing ampicillin. The optimal induction temperature for expressing pIFN-δ5 in the prokaryotic expression system is determined to be 37° C. for 4 hours (h) and the concentration of IPTG is 0.8 millimolar (mM).

The positive clone BL21(DE3) containing pET-pIFN-δ5 is amplified and cultured until the bacteria reach the logarithmic growth phase with an $OD_{600}$ value of around 0.6, at which point the inducer IPTG is added and expression is continued for another 4 h.

Figure 2A:
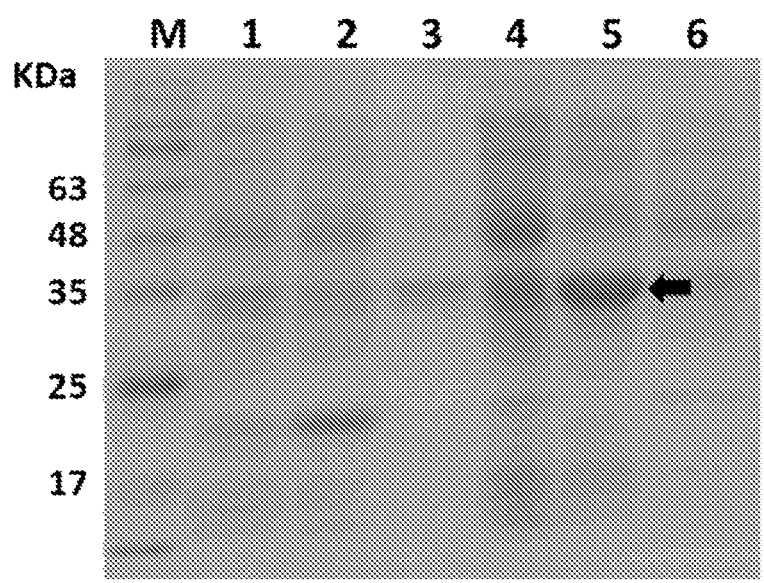
FIG. 2A and FIG. 2B illustrate expression of target protein in Escherichia cob BL21(DE3) transformed with recombinant plasmid vector pET-pIFN-δ5 under induction conditions.
Figure 2B:
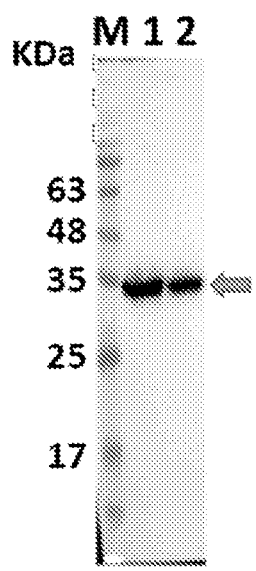

Bacteria after induction culture are collected and fragmented by ultrasound, then the supernatant and inclusion bodies are collected by centrifugation. Sodium dodecyl sulfate polyacrylamide gel electrophoresis (SDS-PAGE) protein electrophoresis shows that protein bands of the expected size (about 35 kilodalton, or kD) appear in the supernatant (see FIG. 2A); and a further detection of western blot on the supernatant sample of the bacteriophage reveals a specific band at the same location (see FIG. 2B).

All the above results suggest that the above constructed pET-pIFN-δ5-containing *Escherichia coli* BL21(DE3) is capable of successfully expressing recombinant pIFN-δ5 and that the target protein exists in the fragmented supernatant of the bacterium.

Embodiment 2 Preparation of pIFN-δ5 Protein in Large Quantities

The positive clone BL21(DE3) containing pET-pIFN-δ5 is expanded to a culture size of 4 litres (L), and the bacteria are collected by centrifugation at the end of the incubation under induction conditions and the bacteria are resuspended in 200 milliliter (mL) Buffer A (containing 20 mM Tris-HCl, 500 mM NaCl, 1 mM PMSF, 5% glycerol, pH 7.5).

The resuspended bacteria are fragmented 3 times under high pressure of 700 Bar, centrifuged at 13,000 revolutions per minute (rpm) for 30 min to collect the supernatant after centrifugation.

The collected supernatant is flowed through a Ni column (His Trap™ HP, which is a ready to use HiTrap™ column, prepacked with precharged Ni Sepharose™ High Performance), equilibrated using Buffer A and then eluted with Buffer B (containing 20 mM Tris-HCl, 500 mM NaCl, 1 mM PMSF, 250 mM imidazole, 5% glycerol, pH 7.5) to obtain the crude purified protein.

The crude purified protein is then desalted into PBS using a G-25 desalting column, where the protein concentration is determined using the bicinchonininc acid (BCA) method.

Figure 3:
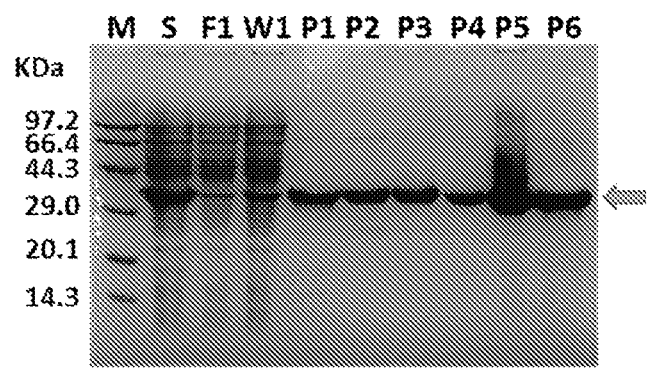
FIG. 3 is a graph showing results after mass expression of pIFN-δ5 protein and purification, where lane M is the protein molecular weight standard, lane S is a supernatant sample from fragmented bacteria cultured under induction conditions, lane F1 is a flow-through sample during the purification, lane Wi is a washout sample during the purification, and lanes P1 to P6 are elution samples during the purification, respectively.

FIG. 3 shows the results of electrophoresis of supernatant samples taken after fragmentation of the bacteria and the purification process, where lane M is the protein molecular weight standard, lane S is a supernatant sample from fragmented bacteria cultured under induction conditions, lane F1 is a flow-through sample during the purification, lane Wi is a washout sample during the purification, and lanes P1 to P6 are elution samples during the purification, respectively.

From the results in FIG. 3, it can be seen that the pET-pIFN-δ5-containing positive clone BL21(DE3) constructed in Embodiment 1 can be used to easily prepare large amounts of highly pure recombinant pIFN-δ5 protein, providing a foundation for its use as a raw material in preparing new drugs or formulations for the inhibition of the causative agent of porcine viral diarrhea.

Embodiment 3 Inhibition of Porcine Diarrhea-Associated Virus Activity by pIFN-δ5 Protein IPECJ2 cells, ST cells, LLC-PK1 cells and MA104 cells are respectively treated with purified pIFN-δ5 protein (at a concentration of 50 ng/mL) for 12 h and then inoculated with PEDV for IPEC-J2 cells, porcine transmissible gastroenteritis virus (TGEV) for ST cells, porcine delta coronavirus (PDCoV) for LLC-PK1 cells and porcine rotavirus (PRoV) for MA104 cells, all at a dose of 0.1 MOI. For ease of description, these experimental groups treated with purified pIFN-δ5 protein and then inoculated with the corresponding virus are referred to as the pIFN-δ5-treated groups, and a control group without pIFN-δ5 protein treatment and inoculated with virus only and a blank group without either pIFN-δ5 protein treatment or virus inoculation are also established.

The virus-inoculated cells are incubated separately for 24 h, and the total RNA is extracted from the cells and the virus copy number in the cell samples is measured.

Figure 4:
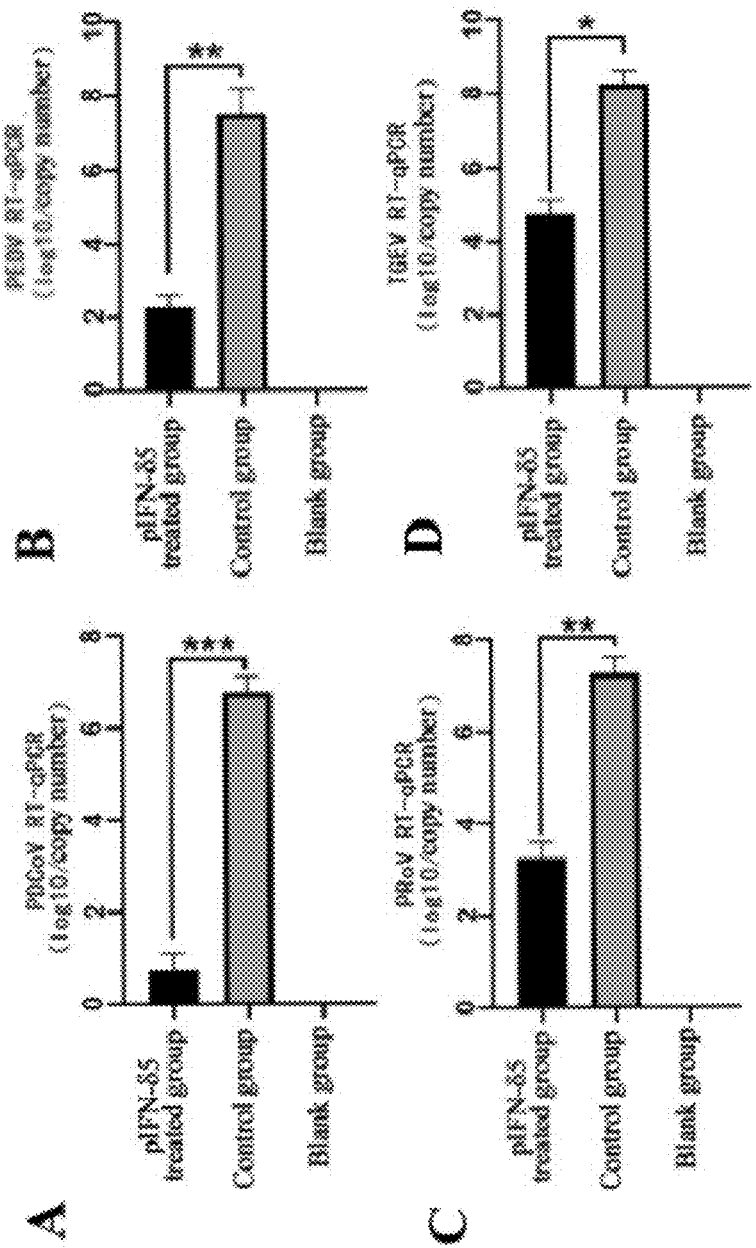
FIG. 4 (including sub-figures. 4A, 4B, 4C and 4D) is a graph showing results of pIFN-δ5 protein inhibition of porcine viral diarrheal pathogens, where a pIFN-δ5 treated group is a group treated with pIFN-δ5 protein and inoculated with virus, a control group is inoculated with virus alone and a blank group is neither treated with protein nor inoculated with virus, wherein subfigure. 4A illustrates the copy numbers of PEDV in control group, blank group and pIFN-δ5 treated group; subfigure. 4B illustrates the copy numbers of TGEV in control group, blank group and pIFN-δ5 treated group; subfigure. 4C illustrates the copy numbers of PDCoV in control group, blank group and pIFN-δ5 treated group; and subfigure. 4D illustrates the copy numbers of PRoV in control group, blank group and pIFN-δ5 treated group.

The results are shown in FIG. 4, where a significant reduction in the copy number of PEDV, TGEV, PDCoV and PRoV viruses is observed in the pIFN-δ5 treated groups compared to that of the control group treated with the inoculated virus alone, indicating that pIFN-δ5 has excellent viral inhibitory activity. Moreover, a new drug or formulation for the inhibition of viral diarrhea causative agents in swine is available using the pIFN-δ5 protein prepared by the method of the present application.

The present application provides a detailed description and illustration of the embodiments in conjunction with the accompanying drawings of the specification, but it should be understood by those skilled in the art that the above embodiments are only preferred embodiments of the present application and that the exhaustive description is only intended to facilitate a better understanding of the spirit of the present application by the reader and do not limit the scope of protection of the present application; any improvements or modifications based on the inventive spirit of the present application should fall within the scope of protection of the present application.

What is claimed is:

1. A method of treating a swine with a porcine-derived interferon-δ5 for inhibiting pathogens of porcine viral diarrhea, comprising: administering to the swine the porcine-derived interferon-δ5;

wherein the pathogens of porcine viral diarrhea comprise one or more selected from the group consisting of porcine epidemic diarrhea virus (PEDV), porcine transmissible gastroenteritis virus (TGEV), porcine delta coronavirus (PDCoV) and porcine rotavirus (PRoV); and the porcine-derived interferon-δ5 comprises an amino acid sequence as set forth in SEQ ID NO: 2.

* * * * *